(12) United States Patent
Acree et al.

(10) Patent No.: US 9,642,570 B2
(45) Date of Patent: May 9, 2017

(54) MULTI-MODAL OLFACTOMETER

(71) Applicants: Terry E. Acree, Geneva, NY (US);
Stephen G. Wyckoff, Geneva, NY (US)

(72) Inventors: Terry E. Acree, Geneva, NY (US);
Stephen G. Wyckoff, Geneva, NY (US)

( * ) Notice: Subject to any disclaimer, the term of this patent is extended or adjusted under 35 U.S.C. 154(b) by 269 days.

(21) Appl. No.: 14/703,632

(22) Filed: May 4, 2015

(65) Prior Publication Data

US 2016/0327531 A1    Nov. 10, 2016

(51) Int. Cl.
*B05B 12/14* (2006.01)
*A61B 5/00* (2006.01)
*G01N 33/00* (2006.01)
*B05B 11/00* (2006.01)

(52) U.S. Cl.
CPC ........ *A61B 5/4011* (2013.01); *B05B 11/3084* (2013.01); *B05B 12/1463* (2013.01); *B05B 12/1472* (2013.01); *G01N 33/0001* (2013.01); *B05B 11/3002* (2013.01); *B05B 11/3015* (2013.01)

(58) Field of Classification Search
CPC . A61B 5/4011; A61M 11/006; A61M 11/008; A61M 11/00; G01N 33/0001; B05B 12/14; B05B 12/1463; B05B 12/1472; B05B 11/3002; B05B 11/3015; B05B 11/3084

See application file for complete search history.

(56) References Cited

U.S. PATENT DOCUMENTS

| 3,618,359 A | * | 11/1971 | Randebrock et al. ........................ G01N 33/0001 73/23.2 |
| 3,674,207 A | * | 7/1972 | Carbonetti, Jr. .... B05B 12/1472 118/323 |
| 3,885,550 A | | 5/1975 | MacLeod |

(Continued)

OTHER PUBLICATIONS

Kurtz, Anne J., "The Role of Color, Congruency, Object Shape and Signal Strength in Bimodal Olfactory and Visual Interactions" —A Dissertation Presented to the Faculty of the Graduate School of Cornell University in Partial Fulfillment of the Requirements for the Degree of Doctor of Philosophy, May 2012, United States.

*Primary Examiner* — Justin Olamit
(74) *Attorney, Agent, or Firm* — Woods Oviatt Gilman LLP; Dennis B. Danella, Esq.

(57) ABSTRACT

A multi-modal olfactometer including a carrier assembly slidably coupled with a track and movable between a loading and testing position, a distribution block coupled with the carrier assembly and including a plurality of independent flow channels, a plurality of bottles configured for containing a gas stimuli and for being coupled with the distribution block, a plurality of tubes in flow communication with corresponding channels defined in the distribution block, an outlet piece including a plurality of independent flow channels that are each in flow communication with one of the respective tubes, and at least one actuator positioned adjacent to the bottles when the carrier assembly is in the testing position. The actuator operates to impact each of the bottles to cause the respective gas stimulus to flow through (Continued)

the respective channel in the distribution block, tube, and channel in the outlet piece for inhalation by a test subject.

26 Claims, 11 Drawing Sheets

(56) References Cited

U.S. PATENT DOCUMENTS

| | | | |
|---|---|---|---|
| 3,902,851 A | 9/1975 | Dravnieks | |
| 4,265,248 A * | 5/1981 | Chuiton | A61B 5/08 600/303 |
| 4,934,386 A * | 6/1990 | Walker | A61B 5/087 131/329 |
| 5,591,409 A | 1/1997 | Watkins | |
| 5,724,256 A | 3/1998 | Lee et al. | |
| 5,767,385 A * | 6/1998 | Bundy | G01N 1/26 73/23.34 |
| 6,067,842 A | 5/2000 | Gygax et al. | |
| 6,325,475 B1 * | 12/2001 | Hayes | A61B 5/00 128/203.11 |
| 6,338,715 B1 | 1/2002 | Hayes et al. | |
| 6,390,453 B1 | 5/2002 | Frederickson et al. | |
| 6,542,442 B2 | 4/2003 | Kaslon | |
| 6,619,559 B2 | 9/2003 | Wohrle | |
| 6,654,664 B1 | 11/2003 | Chiao et al. | |
| 6,712,287 B1 | 3/2004 | Le Pesant et al. | |
| 6,802,460 B2 | 10/2004 | Hess et al. | |
| 6,994,328 B2 | 2/2006 | Watkins et al. | |
| 7,152,758 B2 | 12/2006 | Fazzio et al. | |
| 7,514,048 B2 | 4/2009 | Gau et al. | |
| 8,196,902 B1 | 6/2012 | Pystin | |
| 8,469,293 B2 * | 6/2013 | Doty | A61L 9/122 239/44 |
| 8,821,802 B2 | 9/2014 | Haran | |
| 2007/0295327 A1 | 12/2007 | Bottomley | |
| 2012/0184828 A1 | 7/2012 | Lundstrom et al. | |
| 2014/0319238 A1 * | 10/2014 | Su | A45D 34/00 239/70 |

\* cited by examiner

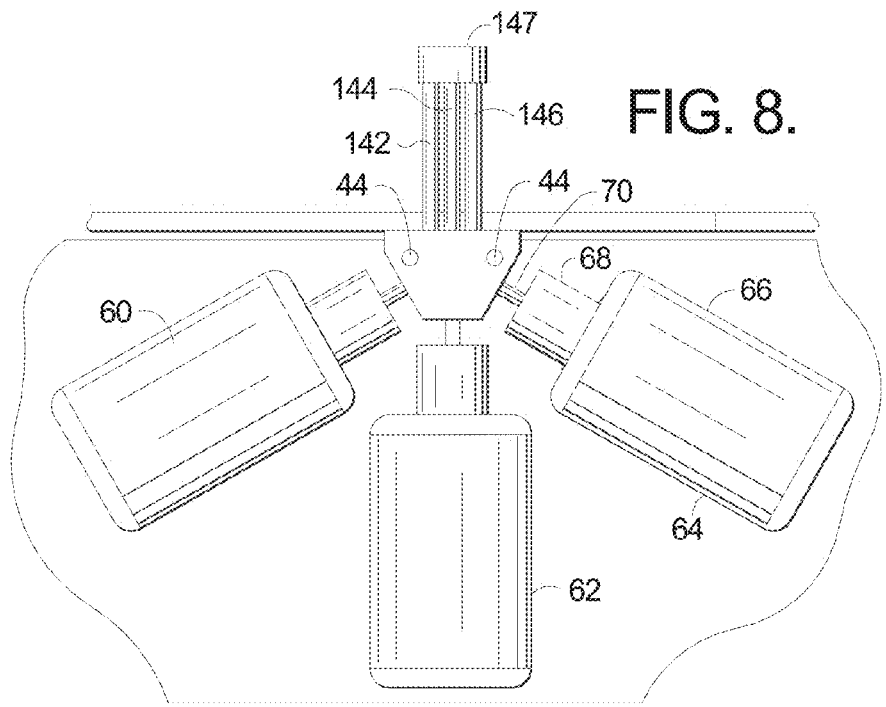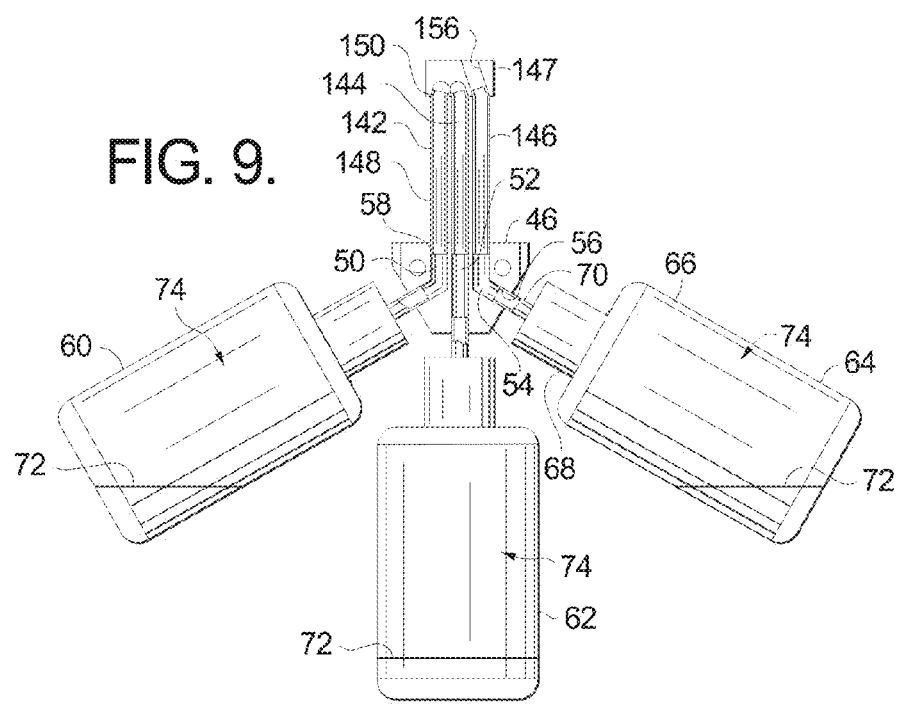

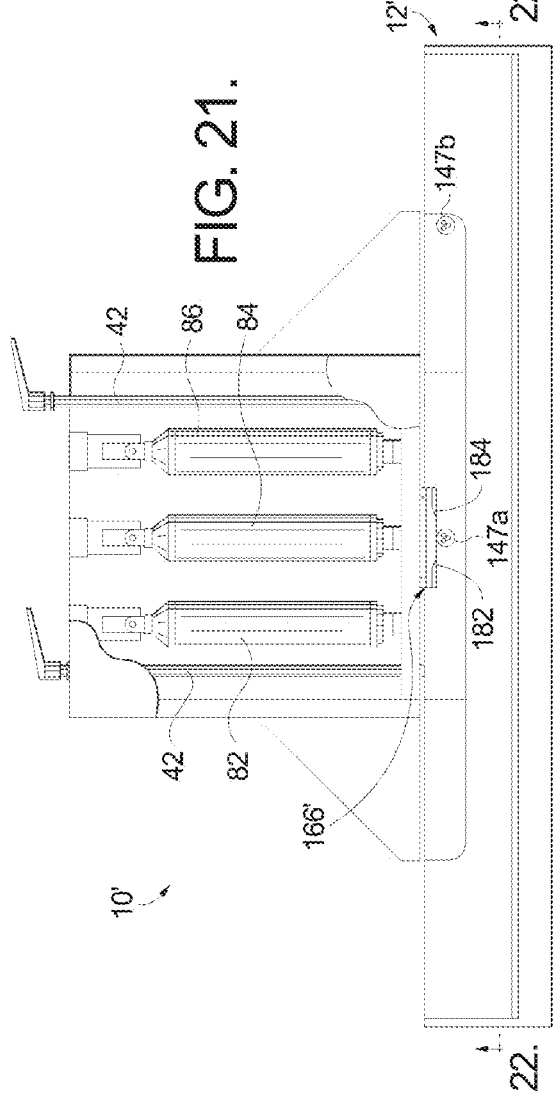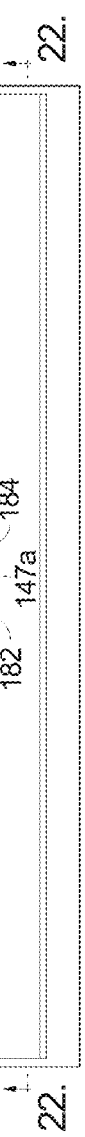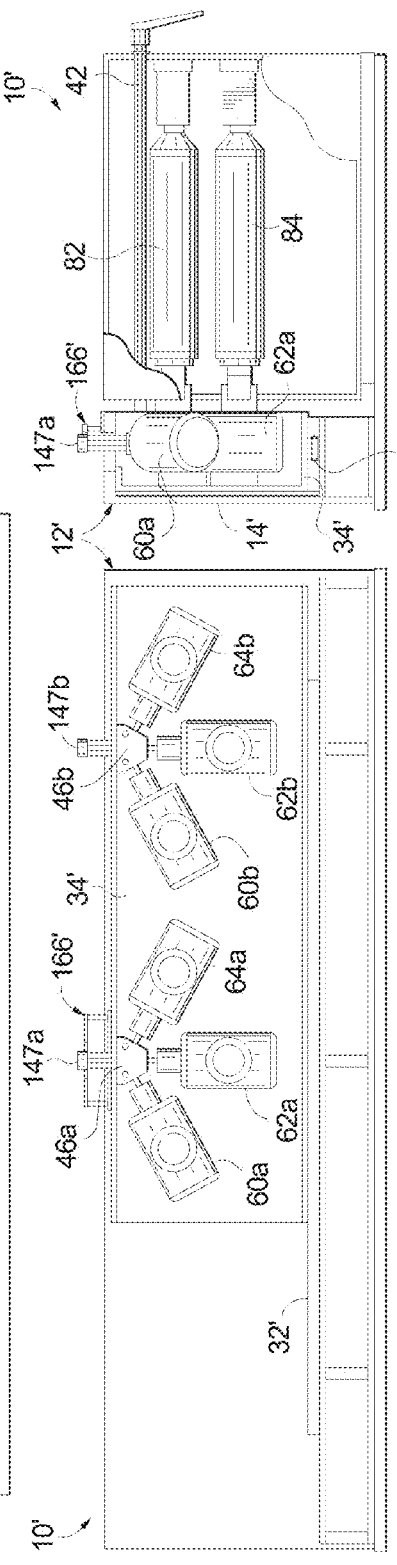

MULTI-MODAL OLFACTOMETER

FIELD OF THE INVENTION

The present invention relates to a multi-modal olfactometer; in particular, the present invention relates to an olfactometer comprising a plurality of bottles connected to independent distribution flow channels defined in a distribution block, and separate tubing connecting to each of the independent distribution flow channels to an outlet piece, wherein a consistent amount of gas stimulus contained within one of the bottles is selectively discharged through the outlet piece using at least one actuator for inhalation by a test subject. The bottles can be easily and quickly removed from the distribution block and easily interchanged for rapid testing of different gas stimuli, while eliminating cross-contamination through the use of the independent flow channels and separate replaceable tubing. The olfactometer may also include a computing device that selectively operates the at least one actuator to coordinate the release of the gas stimulus from one of the bottles and the inhalation of the gas stimulus by the test subject in conjunction with a visual and/or audio cue.

BACKGROUND OF THE INVENTION

In general, an olfactometer is a device that is used to produce odors in a precise and controlled manner so that olfactory thresholds and intensities for different stimuli can be measured. Olfactometers have been used for many years in a laboratory environment to conduct qualitative experiments using human subjects for market research in many different types of products, such as, but not limited to, foods, drinks, and perfumes. The information obtained through these experiments is valuable because it allows the manufacturer of such products to optimize the amount of odor producing stimulant included in the product to produce a desired result.

One common type of instrument that is used to study olfaction is a dilution olfactometer. Initially, the dilution olfactometer was used to determine the concentration at which an odor was detectable (i.e., threshold), but has more recently been used to also study a wide range of psycho-physical questions. In operation, the dilution olfactometer is used to dilute a sample gas containing a stimulant with a clean gas (e.g., air or nitrogen) at various flow rates. The required blending of the sample gas and clean gas makes it challenging to optimize the flow of these gases in a repeatable and contamination-free manner. The difficulty in achieving repeatable results is made more difficult given that the sample gas is mixed with the clean gas in varying amounts so that threshold levels may be tested.

There have been attempts to provide improvements to the existing dilution olfactometer by providing various solutions for changing the concentration of the dilution flow, improving changeover time, and reducing contamination. However, the need to uniformly blend sample gas with clean gas inherently requires a fairly complex plumbing system and other flow control mechanisms, which increases the cost of manufacturing these types of devices.

Accordingly, there exists a need for an olfactometer that produces test samples that have a consistent concentration, provides a simple construction that reduces the possibility of cross-contamination, allows for the testing of multiple stimulants at a time, and allows for the rapid interchangeability of samples during the testing process. The present invention fills these, as well as other, needs.

SUMMARY OF THE INVENTION

The present invention is directed to a multi-modal olfactometer that operates to selectively discharge a gas stimulus to a test subject for inhalation. The olfactometer set forth herein provides a number of advantages and addresses some of the drawbacks associated with existing olfactometers. For example, the olfactometer described herein allows for the rapid, efficient, consistent and repeatable delivery of a gas stimulus to a test subject, while essentially eliminating any cross-contamination that may occur during the process. This and other advantages will be evident in view of the disclosure set forth herein.

In particular, one aspect of the present invention is directed to an olfactometer device comprising a track, and a carrier assembly slidably coupled with the track, wherein the carrier assembly is configured for moving between a first position and a second position. The device further includes a distribution block coupled with the carrier assembly, wherein the distribution block includes a first distribution channel and a second distribution channel defined therein. Each of the first and second distribution channels include an inlet opening and an outlet opening, wherein the first distribution channel is independent of the second distribution channel. A first bottle may be included and is configured for containing a first gas stimulus. The first bottle includes an outlet opening configured for being coupled with the inlet opening of the first distribution channel. A second bottle may also be included and is configured for containing a second gas stimulus. The second bottle includes an outlet opening configured for being coupled with the inlet opening of the second distribution channel. The device may further comprise a first tube including a first end and a second end, wherein the first end of the first tube is connected to the outlet opening of the first distribution channel of the distribution block. The device may further include a second tube that has a first end and a second end, wherein the first end of the second tube is connected to the outlet opening of the second distribution channel of the distribution block. In addition, an outlet piece includes a first outlet channel and a second outlet channel defined therein that are independent of one another. The second end of the first tube is connected to the first outlet channel of the outlet piece, and the second end of the second tube is connected to the second outlet channel of the outlet piece. At least one actuator is positioned adjacent to the first and second bottles when the carrier assembly is in the second position. It is also contemplated that separate actuators be used for each bottle. The at least one actuator is configured for selectively impacting either the first or second bottle when the carrier assembly is in the second position. When the first bottle is impacted by the at least one actuator, the first gas stimulus flows through each of the first distribution channel in the distribution block, the first tube, and the first outlet channel in the outlet piece for inhalation by a test subject. When the second bottle is impacted by the at least one actuator, the second gas stimulus flows through each of the second distribution channel in the distribution block, the second tube, and the second outlet channel in the outlet piece for inhalation by the test subject. In one example, the actuator may impact the respective bottle for about 0.071 seconds.

In another aspect, the device may further comprise a computing device including a memory, wherein the computing device is in communication with the at least one actuator. Further, an application program is stored in the memory of the computing device, and is configured for transmitting an actuation signal to the at least one actuator to selectively impact the respective bottle. The computing device may further include a monitor, wherein the application program is further configured for providing at least one visual cue using the monitor prior to transmitting the actuation signal to the at least one actuator. The computing device may further include a speaker, wherein the application program is configured for providing at least one audio cue using the speaker prior to transmitting the actuation signal to the at least one actuator.

In yet another aspect, the outlet piece includes a longitudinal axis, wherein each of the channels defined in the outlet piece are disposed at about a 15 degree angle relative to the longitudinal axis. The device may also comprise a housing including a front wall, wherein the track is coupled to the housing and positioned at an angle of, for example, 3 degrees, relative to the front wall of the housing. A locking pin may also be slidably coupled with the housing so that it can selectively engage the carrier assembly when the carrier assembly is in the second testing position.

In another aspect, an assembly may be mounted on the top wall of the housing and adjustably positioned to engage the outlet piece when the carrier assembly is moved toward the second position to properly position the outlet piece relative to the test subject's nose. In particular, the assembly may comprises a base plate configured for being mounted to the top wall of the housing, a support coupled with the base plate, and a portion coupled with the support. The portion includes a first tapered surface configured for engaging the outlet piece when the carrier assembly is moved toward the second position. The base plate may have at least one elongated slot defined therein configured for receiving a fastener for adjustably mounting the assembly on the top wall of the housing.

In another aspect, the device may further comprise at least one mounting pin extending from the carrier assembly, wherein the distribution block includes a corresponding number of apertures configured for receiving the at least one mounting pin to couple the distribution block to the carrier assembly. The first bottle and the second bottle may be directly or indirectly connected to the distribution block. The bottles and tubes may be formed of perfluoroalkoxy alkane (PFA), as well as other materials described herein.

In yet another aspect, an alternative olfactometer is provided that includes two sets of bottles that are connected to two different distribution blocks, tubes and outlet pieces that are mounted to the carrier assembly. Utilizing two sets of bottles on the carrier assembly allows one set of bottles to be loaded with volatile aromatic solution in the first position, while the other set of bottles are being used to conduct the testing of gas stimuli. This configuration increases the efficiency at which the testing process can be conducted. An alternative assembly may be utilized with this configuration to provide for the proper positioning for each outlet piece as the carrier assembly is moved between the first and second positions.

Additional objects, advantages and novel features of the present invention will be set forth in part in the description which follows, and will in part become apparent to those skilled in the art, when considered with the attached figures.

BRIEF DESCRIPTION OF THE DRAWINGS

The accompanying drawings form a part of the this specification and are to be read in conjunction therewith, wherein like reference numerals are employed to indicate like parts in the various views, and wherein:

FIG. 8 is a partial view of a plurality of bottles connected to a distribution block, tubing, and an outlet piece;

FIG. 9 is a view similar to FIG. 8 showing the distribution block, tubing, and the outlet piece in cross-section;

FIG. 21 is a top view with portions broken away and removed of an olfactometer in accordance with another aspect of the present invention;

FIG. 22 is a back view of the olfactometer shown in FIG. 21 in the loading position;

FIG. 23 is a right side view of the olfactometer shown in FIG. 21;

DETAILED DESCRIPTION OF THE INVENTION

Figure 1:
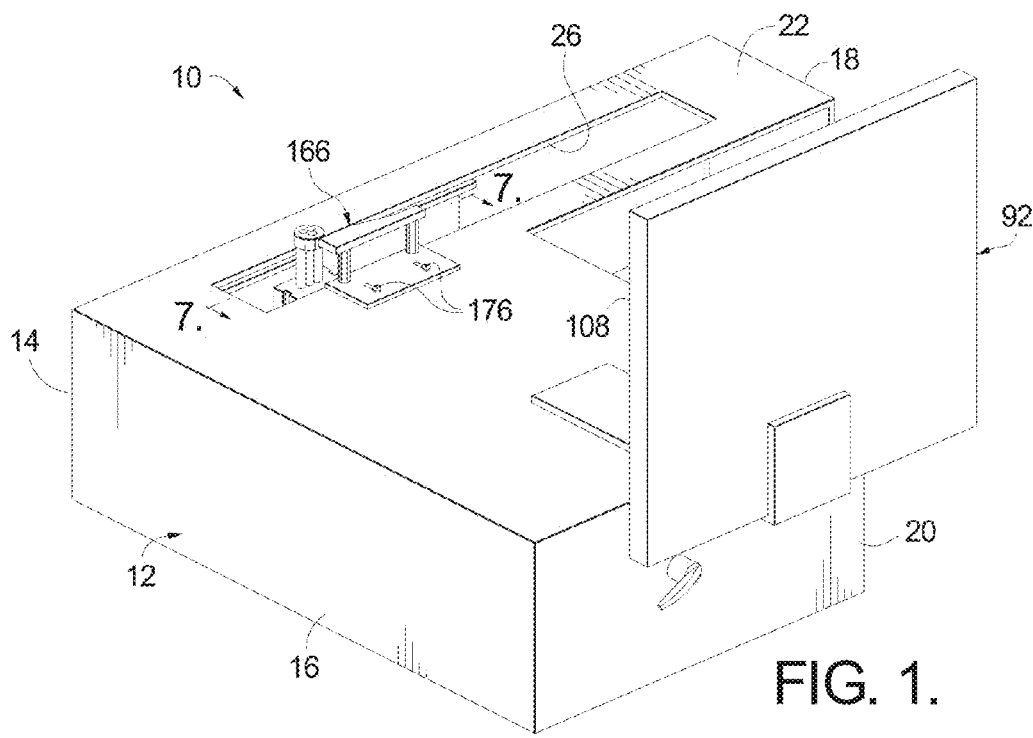
FIG. 1 is a perspective view of an olfactometer in accordance with one aspect of the present invention.
Figure 2:
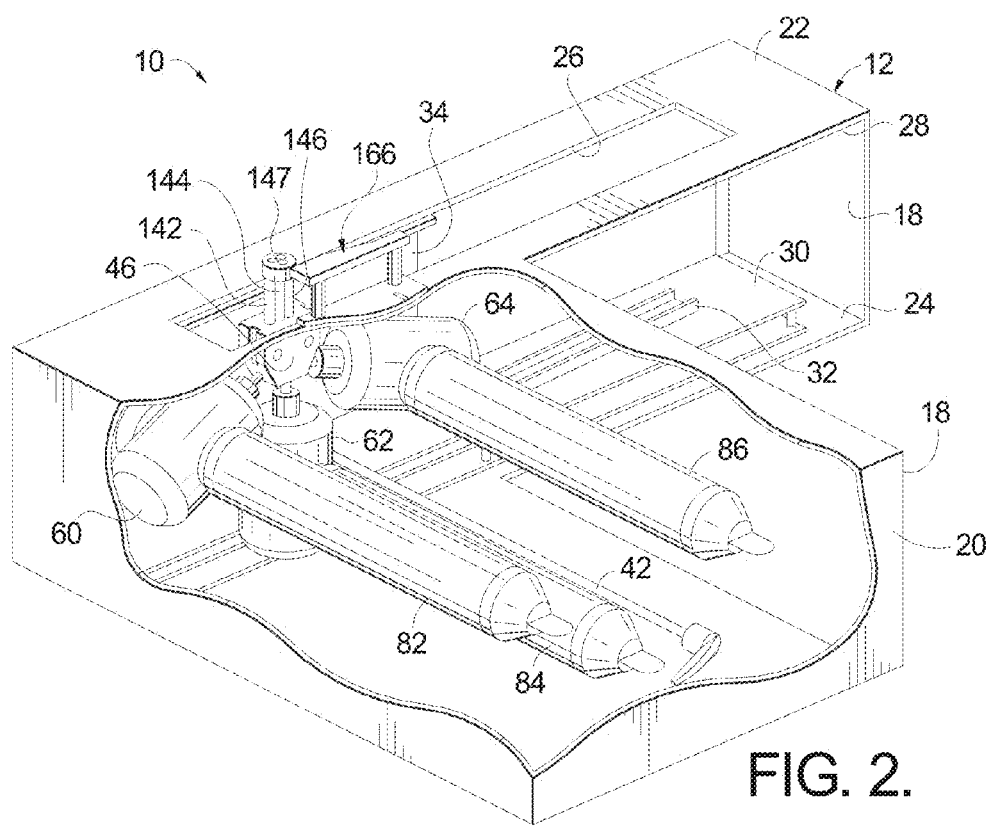
FIG. 2 is a perspective view similar to FIG. 1 with a portion broken away and removed to show certain components located within a housing of the olfactometer.

Referring now to the drawings in detail and initially to FIG. 1, reference numeral 10 designates a multi-modal olfactometer in accordance with one aspect of the present invention. In general, and as described in more detail below, olfactometer 10 is used to conduct qualitative experiments with a test subject, such as, for example, a human test subject, to measure olfactory thresholds and intensities for different gas stimuli. Olfactometer 10 includes a number of features that allow for the efficient and repeatable testing of a plurality of different gas stimuli based on volatile aromatic solutions, while eliminating the occurrence of cross-contamination during the testing process. Further, olfactometer 10 is configured to provide for multi-modal testing by incorporating visual and/or auditory cues in conjunction with the delivery of the gas stimuli to the test subject, which not only coordinates the inhalation by the test subject with the delivery of the gas stimuli, but also expands the potential multi-modal experimental opportunities.

As best seen in FIGS. 1-4, olfactometer 10 includes a housing 12 that may be configured to operate as a bench-top unit so that the test subject can position his or her nose in the appropriate location for inhalation. Housing 12 includes a front wall 14, side walls 16, 18, back wall 20, top wall 22, and a bottom wall 24. An elongated slot 26 is defined in top wall 22 of housing 12, and an access opening 28 is provided in the rear portion of housing 12. A platform 30 may be disposed on bottom wall 24 and extend a substantial portion of the length of housing 12. A track 32 may either be disposed on platform 30 or directly mounted to bottom wall 24 if platform 30 is not used.

Figure 3:
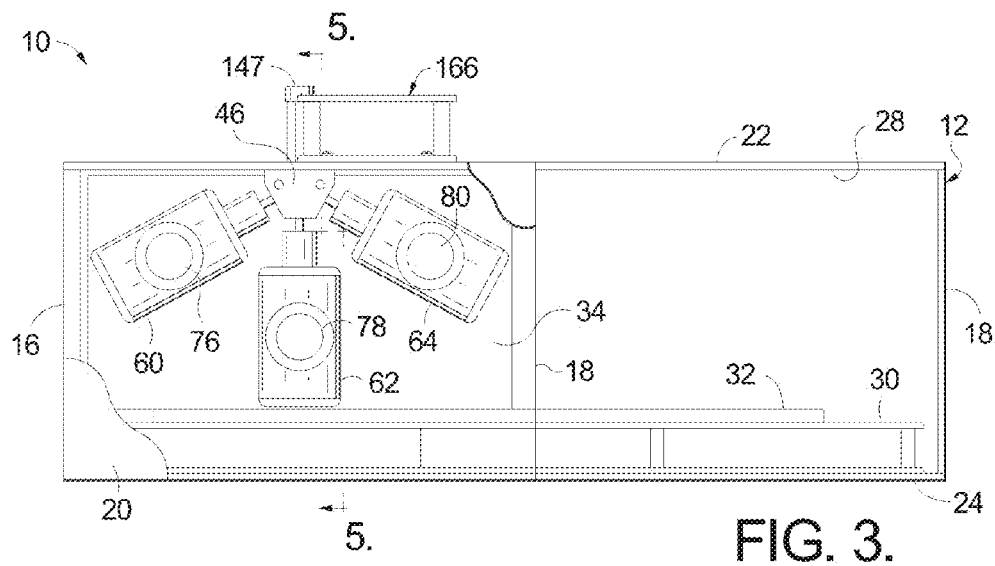
FIG. 3 is a rear view of the olfactometer shown in FIG. 1 with a portion broken away and removed to show a carrier assembly in a testing position.
Figure 4:
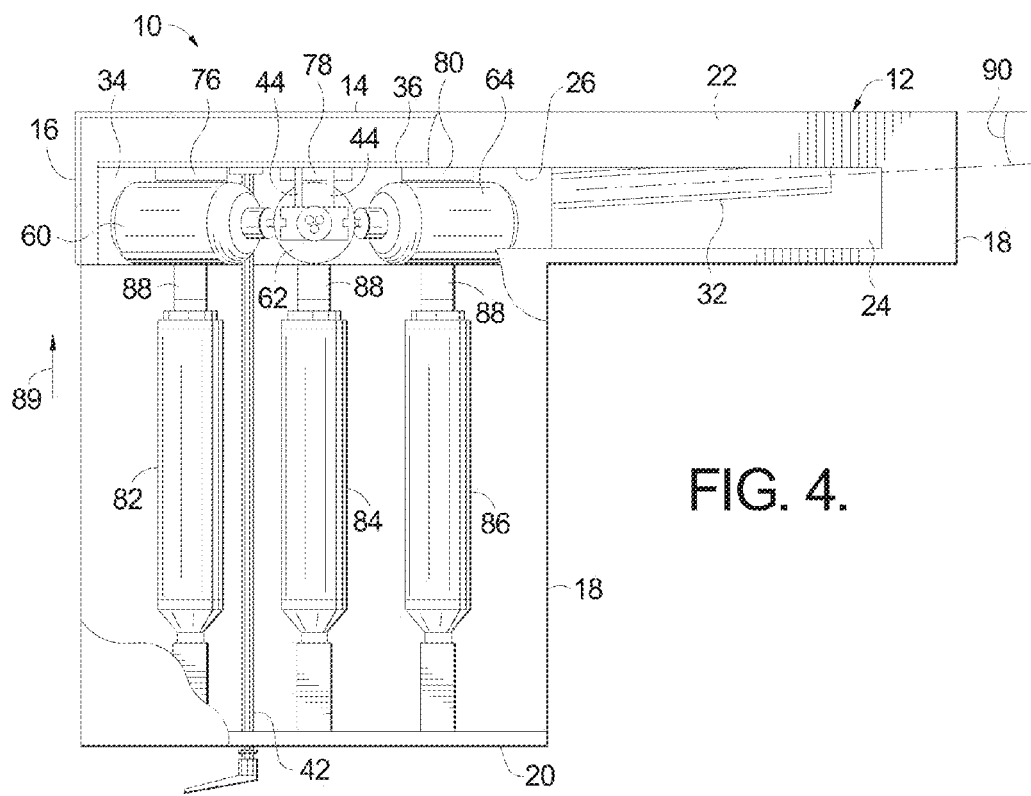
FIG. 4 is a top view of the olfactometer shown in FIG. 1 with a portion broken away and removed to show the carrier assembly in the testing position.
Figure 5:
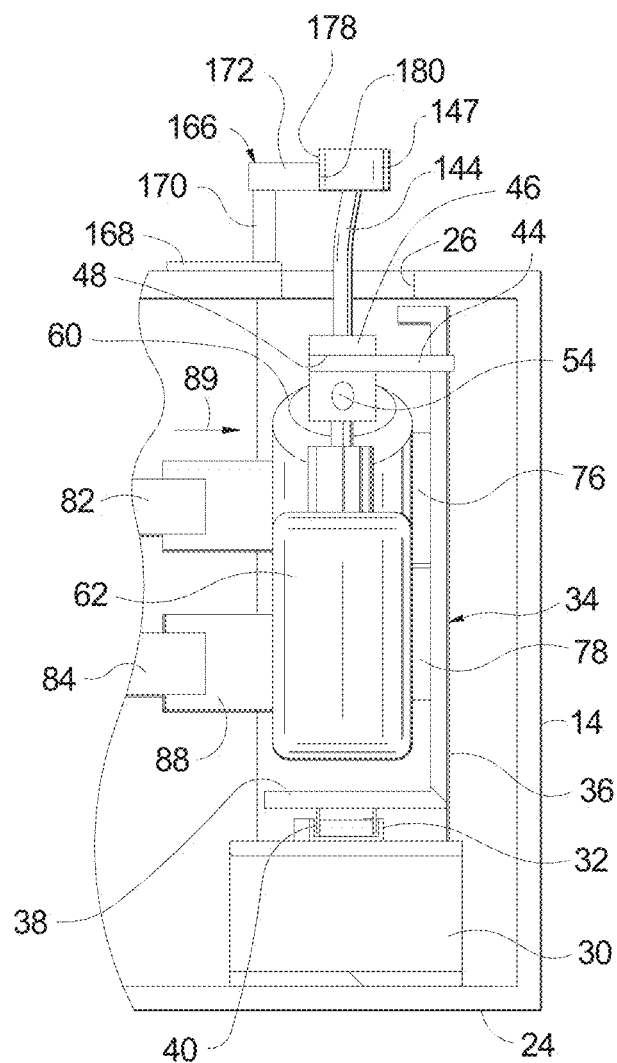
FIG. 5 is a cross-sectional view taken along line 5-5 in FIG. 3.

As best seen in FIGS. 2-7, a carrier assembly 34 is slidably coupled with track 32 so that carrier assembly 34 may be selectively moved between a first loading position (FIGS. 6 and 7) and a second testing position (FIGS. 1-4). With particular reference to FIG. 5, carrier assembly 34 includes a rear wall 36 and a bottom wall 38, wherein a guide 40 is coupled with bottom wall 38 to slidably couple carrier assembly 34 with track 32. A locking pin 42 may be slidably coupled with back wall 20 of housing 12 and positioned to selectively engage rear wall 36 to maintain the position of carrier assembly 34 when carrier assembly 34 is in the second testing position. Further, at least one mounting pin 44 is coupled with, and extends outwardly from, rear wall 36 and is adapted to mount a distribution block 46 to carrier assembly 34.

As best seen in FIGS. 5 and 14-16, distribution block 46 includes one or more apertures 48 defined therein configured for receiving a corresponding number of mounting pins 44 to couple distribution block 46 to carrier assembly 34. Therefore, distribution block 46 moves along with carrier assembly 34 as carrier assembly 34 is moved between the first loading position and the second testing position. However, it should be understood that distribution block 46 may optionally be decoupled from carrier assembly 34 by sliding distribution block 46 off of the at least one mounting pin 44. Distribution block 46 further includes a plurality of independent distribution channels 50, 52, 54 defined therein that are used to allow for the flow of gas stimuli, which will be described further below. Distribution channels 50, 52, 54 are described as being independent of each other because they do not allow for gas stimulus flowing through one of the channels to flow into another channel. Further, each of the distribution channels 50, 52, 54 include an inlet opening 56 and an outlet opening 58. Distribution channels 50, 52, 54 may extend in any number of different directions through distribution block 46. However, it is contemplated that the length of each distribution channel 50, 52, 54 be minimized. As seen in FIG. 9, inlet opening 56 for each distribution channel 50, 52, 54 is configured for being directly or indirectly coupled with a corresponding bottle 60, 62, 64. It can been seen in FIG. 15 that the configuration of distribution channel 52 may be linear, while distribution channels 50, 54 may be configured at an obtuse angle to minimize the size of distribution block 46 and allow bottles 60, 62, 64 to be connected to distribution block 46. In one example shown in FIG. 9, bottles 60, 64 connected to distribution channels 50, 54, respectively, may be disposed at approximately a 90 degree angle relative to one another.

As best seen in FIGS. 8 and 9, each bottle 60, 62, 64 includes a container portion 66 and a cap 68. Cap 68 includes an outlet opening 70 nozzle configured to be easily connected to and removed from inlet opening 56 of each respective distribution channel 50, 52, 54 when carrier assembly 34 is in the loading position. For example, and with specific reference to FIG. 9, outlet opening 70 may be configured to be press-fit within inlet opening 56, however it should be understood that other types of configurations for connecting outlet opening 70 and inlet opening 56 are contemplated. Bottles 60, 62, 64 may be formed of any type of flexible material that is capable of containing a volatile aromatic solution 72 and corresponding gas stimulus 74 within container portion 66, and expelling the gas stimulus from outlet opening 70 at a high velocity when impacted, for example, approximately 30 miles per hour. For example, container portion 66 of bottles 60, 62, 64 may be formed of perfluoroalkoxy alkane (PFA), polytetrafluoroethylene (PTFE), and the like. Further, as best seen in FIGS. 4 and 5, a backer block 76, 78, 80 is mounted to rear wall 36 of carrier assembly 34 and disposed adjacent to a respective bottle 60, 62, 64 to stabilize the position of each bottle 60, 62, 64 relative to carrier assembly 34 when impacted by an associated actuator 82, 84, 86.

As best seen in FIG. 4, each of actuators 82, 84, 86 are mounted to housing 12 and have an impact end 88 that is positioned adjacent to the first and second bottles when the carrier assembly is in the second testing position. Moreover, each of actuators 82, 84, 86 is configured for being activated to selectively impact the respective adjacent bottle 60, 62, 64 by moving impact end 88 in a rapid manner in a direction 89 when carrier assembly 34 is in the second testing position, and then returning impact end 88 to its original position to get ready for subsequent testing. Each actuator 82, 84, 86 operates to drive a piston, and therefore impact end 88, a controlled rate and controlled distance, for example, about one inch. In one aspect, track 32 may be disposed at an angle 90 relative to front wall 14 of housing 12, for example, at a 3 degree angle relative to front wall 14 in order to position bottles 60, 62, 64 closer to the impact end 88 of the respective actuator 82, 84, 86 as carrier assembly 34 moves from the first loading position (FIGS. 6 and 7) to the second testing position (FIGS. 8 and 4). While the depicted version of olfactometer 10 includes three actuators 82, 84, 86, it should be understood that olfactometer 10 may include a single actuator, or any number of actuators that corresponds to the number of bottles that may be connected to distribution block 46. Regardless of the number of actuators used in olfactometer 10, the impact on a bottle by the respective actuator may be selectively initiated by generating an activation signal using either a manual switch on the respective actuator, or a computing device 92 executing an olfactory testing application program stored in a memory 94 of computing device 92 that transmits the activation signal to the respective actuator.

Figure 27:
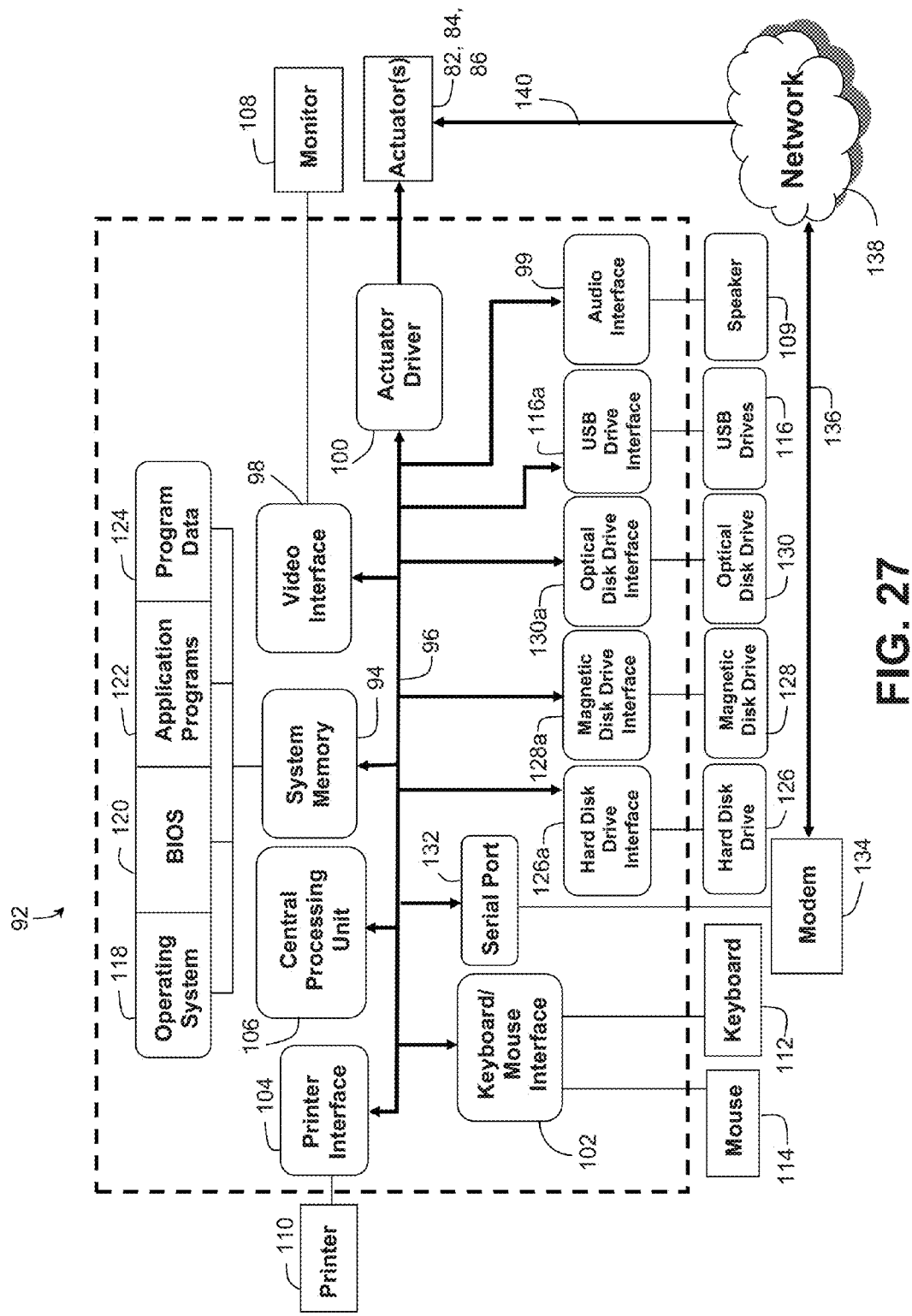
FIG. 27 is a schematic view of an exemplary computing device that may be used in conjunction with the present invention.

FIG. 27 shows an exemplary computing device 92 that can be used to produce the activation signal that causes actuators 82, 84, 86 be selectively activated to impact a respective bottle 60, 62, 64 during the testing process.

Computing device 92 may comprise a system bus 96 that couples a video interface 98, an audio interface 99, an actuator driver 100, a keyboard/mouse interface 102, a printer interface 104, and memory 94 to a Central Processing Unit (CPU) 106. A monitor or display 108 may be connected to bus 96 by video interface 98 and provides the user with a graphical user interface to view at least one visual cue generated by the olfactory testing application program prior to the actuation signal being transmitted to a selected actuator 82, 84, 86 to prompt the test subject to inhale the gas stimuli. Further, a speaker 109 may be connected to bus 96 by audio interface 99 and provides the user with at least one audio cue generated by the olfactory testing application program prior to the actuation signal being transmitted to a selected actuator 82, 84, 86 to prompt the test subject to inhale the gas stimuli. The audio and visual cue may be used alone or in combination with each other to provide for a multi-modal test experiment. Each of actuators 82, 84, 86 is in communication with computing device through actuator driver 100, wherein actuator driver 100 operates to transmit the activation signal to the selected actuator 82, 84, 86. The printer interface 104, for example, allows for a printer 110 to produce a printout of one or more aspects of the olfactory test provided to a test subject. The graphical user interface allows the test subject to enter commands and information into computing 92 to either start the olfactory test, proceed through the test protocol, or finish the test using a keyboard 112 and a user interface selection device 114, such as a mouse or other pointing device, or using a touch screen system. Keyboard 112 and user interface selection device are connected to bus 96 through keyboard/mouse interface 102. The display 108, keyboard 112, and user interface selection device 114 are used in combination to form the graphical user interface which allows the user to implement at least a portion of the present invention. Other peripheral devices may be connected to computing device 92 through universal serial bus (USB) drives 116 to transfer information to and from computer 92. For example, a thumb drive may be connected to computer 92 through USB drives 116 so that data representative of an olfactory test protocol may be downloaded to memory 94 or another memory storage device associated with computer 92 such that different multi-modal olfactory tests may be conducted on test subjects using olfactometer 10. It should be understood that computing device 92 described herein may not necessarily include all of the features described herein. For example, computing device 92 may not necessarily include printer 110.

Memory 94 is also connected to bus 96 and may include read only memory (ROM), random access memory (RAM), an operating system 118, a basic input/output system (BIOS) 120, application programs 122 (such as the olfactory testing application program), and program data 124. Computing device 92 may further include a hard disk drive 126 for reading from and writing to a hard disk, a magnetic disk drive 128 for reading from and writing to a removable magnetic disk (e.g., floppy disk), and an optical disk drive 130 for reading from and writing to a removable optical disk (e.g., CD ROM or other optical media). Computing device 92 may also include USB drives 116 and other types of drives for reading from and writing to flash memory devices (e.g., compact flash, memory stick/PRO and DUO, SD card, multimedia card, smart media xD card). A hard disk drive interface 126a, magnetic disk drive interface 128a, an optical drive interface 130a, a USB drive interface 116a, and audio interface 99 operate to connect bus 96 to hard disk drive 126, magnetic disk drive 128, optical disk drive 130, USB drive 116 and speaker 109, respectively. Each of these drive components and their associated computer-readable media may provide computing device 92 with non-volatile storage of computer-readable instruction, program modules, data structures, application programs, an operating system, and other data for computing device 92. In addition, it will be understood that computing device 92 may also utilize other types of computer-readable media in addition to those types set forth herein, such as digital video disks, random access memory, read only memory, other types of flash memory cards, magnetic cassettes, and the like.

Computing device 92 may operate in a networked environment using logical connections with actuators 82, 84, 86. A serial port 132 and a modem 134, or another type of network interface, may provide a communication path 136 between bus 96 and a network 138, which allows, for example, an actuation signal to be communicated 140 from computing device 92 through network 138 to actuators 82, 84, 86 as instructed through the execution of the olfactory testing application program. It will be appreciated that the network connections shown herein are merely exemplary, and it is within the scope of the present invention to use other types of network connections between computer 92 and actuators 82, 84, 86 including both wired and wireless connections.

As best seen in FIGS. 2, 5, 8 and 9, a plurality of tubes 142, 144, 146 are connected to distribution block 46 and are configured for providing a flow path for the fluid communication of gas stimuli 74 originating from a respective bottle 60, 62, 64 to an outlet piece 147. In particular, each tube 142, 144, 146 may be approximately 10 centimeters in length and extend through slot 26 defined in top wall 22 of housing 12. Each tube 142, 144, 146 includes a first end 148 and a second end 150. First end 148 is connected to outlet opening 58 of a respective channel 50, 52, 54 of distribution block 46. For example, and with specific reference to FIG. 9, first end 148 may be configured to be press-fit within outlet opening 58, however it should be understood that other types of configurations for connecting first end 148 and outlet opening 58 are contemplated. It is preferred that tubes 142, 144, 146 may be easily removed from outlet opening 58 so that they can be replaced as needed. Tubes 142, 144, 146 may be formed of any type of material that is capable of allowing gas stimulus 74 to flow therethrough. For example, tubes 142, 144, 146 may be formed of perfluoroalkoxy alkane (PFA), polytetrafluoroethylene (PTFE), and the like. Further, second end 150 of each tube 142, 144, 146 may be connected to outlet piece 147.

As best seen in FIGS. 8-13, outlet piece 147 includes a plurality of independent outlet channels 152, 154, 156 defined therein configured to connect with respective tubes 142, 144, 146 to allow gas stimulus 74 to flow therethrough and disburse gas stimulus 74 to a test subject for inhalation. In particular, as best seen in FIG. 9, second end 150 of each tube 142, 144, 146 is connected to the respective outlet channel 152, 154, 156 of outlet piece 147. As best seen in FIGS. 10-13, outlet piece 147 includes a longitudinal axis 158, and each outlet channel 152, 154, 156 may be oriented at an angle 160, such as, for example, approximately 15 degrees, relative to longitudinal axis 158 so that gas stimuli 74 emitted from each outlet channel 152, 154, 156 toward test subject is directed at a common point 162 located a distance 164 above outlet piece 147. The distance 164 above outlet piece 147 may be, for example, approximately 1 centimeter.

As best seen in FIGS. 1, 3, and 5, an assembly 166 may be mounted on top wall 22 of housing 12 to move outlet piece 147 to an appropriate position to allow the test subject to inhale gas stimulant 74 using his or her nose. With reference to FIGS. 17-20, assembly 166 comprises a base plate 168, at least one upstanding support 170, and a portion 172. Base plate 168 is configured for being mounted to top wall 22 of housing 12, and at least one elongated slot 174 defined therein configured for receiving a fastener 176 (FIG. 1) for adjustably mounting assembly 166 on the top wall 22 of housing 12. As best seen in FIG. 5, the at least one support 170 is coupled with base plate 168 and is adapted to position portion 172 at a height above top wall 22 of housing 12 so that portion 172 can be slidably engaged with an outer surface 178 of outlet piece 147 as carrier assembly 34 is moved toward the second testing position (FIGS. 1-5). In particular and with additional reference to FIGS. 17-20, as the carrier assembly is moved toward the second position, outer surface 178 of outlet piece 147 is placed in contact with a tapered surface 180 that is angled such that tubes 142, 144, 146 bend slightly and outlet piece 147 moves toward the test subject's nose.

Now that the components of olfactometer 10 have been described above, the operation of olfactometer 10 will be discussed. Initially, carrier assembly 34 is placed in the first loading position shown in FIGS. 6 and 7. The container portion 66 of at least two of bottles 60, 62, 64 may be filled with volatile aromatic solution 72, which thereby produces a corresponding gas stimulus 74 disposed in equilibrium within the remaining head space of container portion 66 so that the concentration of gas stimulus 74 is constant. The cap 68 is then coupled with container portion 66. It should be understood that volatile aromatic solution 74 may be the same substance and/or concentration in each of bottles 60, 62, 64, different substances and/or concentration in each of bottles 60, 62, 64, or the substances and/or concentration may be the same in two of bottles 60, 62 and different in the remaining bottle 64. It should also be understood that olfactometer 10 may use any number of bottles therewith. Bottles 60, 62, 64 may then be press-fit into inlet opening 56 of a respective distribution channel 50, 52, 54 of distribution block 46, wherein bottles 60, 62, 64 are disposed adjacent to backer blocks 76, 78, 80, respectively. Assuming tubes 142, 144, 146 have been coupled to outlet opening 58 of each distribution channel 50, 52, 54, and outlet piece 147 has been coupled to each tube 142, 144, 146, carrier assembly 34 may be moved from the first loading position to the second testing position shown in FIGS. 3 and 4.

As carrier assembly 34 is moved from the first loading position to the second testing position, tubes 142, 144, 146 move within slot 26 defined in top wall 22 of housing 12, and outer surface 178 of outlet piece 147 contacts tapered surface 180 of assembly 166. The flexible nature of tubes 142, 144, 146 allows tapered surface 180 to move outlet piece 147 toward a test subject positioned next to front wall 14 of housing 12, as seen in FIG. 5. Furthermore, due to the angled orientation of track 32 relative to front wall 14, bottles 60, 62, 64 are moved in close proximity to impact end 88 of each actuator 82, 84, 86, respectively. Once carrier assembly 34 is in the second testing position, locking pin 42 may be moved in direction 89 to engage carrier assembly 34, thereby preventing carrier assembly 34 from sliding along track 32 during the testing process. In this position, olfactometer 10 is ready to begin the testing process with a test subject.

Next, the olfactory testing application program may be executed using computing device 92 in order to begin the testing process. In particular, the application program includes programmed instructions that may be executed to display one or more visual cues on monitor 108 and/or produce one or more audio cues using speaker 109 to place the test subject on notice as to when a gas stimulus will be emitted from outlet piece 147. For example, a visual cue may be a timer or similar type of indicator, and an audio cue may be a certain sound that the test subject recognizes as an indication that the gas stimulus will be emitted from outlet piece 147. The visual and/or audio cue are intended to coordinate the release of the gas stimulus from outlet piece 147 and the inhalation of the gas stimulus by the test subject. It should be noted that prior to or after filling each of the bottles 60, 62, 64 with volatile aromatic solution 72, computing device 92 may be used to enter the types of volatile aromatic solution 72 placed in each of bottles 60, 62, 64 so that certain testing sequences can be preprogrammed to run automatically using computing device 92. In other words, computing device 92 will be able to provide for the emission of certain gas stimuli in a certain predefined sequence so that the testing process can be conducted in an efficient manner. The olfactory testing application program may also include other types of executable instructions for use with computing device 92 that allows the olfaction testing to be combined with other sensory tests, thereby allowing for additional types of multi-modal experiments.

In coordination with the visual and/or audio cue, the application program operates to execute instructions that generates an actuation signal that is transmitted by actuation driver 100 to one of actuators 82, 84, 86 to impact the respective bottle 60, 62, 64 and release the gas stimulus contained therein. For example, if it is desired to emit the gas stimulus 74 contained in bottle 60, an actuation signal would be transmitted to actuator 82 thereby causing impact end 88 to move in direction 89 about one inch, for example, to impact bottle 60. When bottle 60 is impacted, bottle 60 may be temporarily deformed so that gas stimulus 74 is forced out of outlet opening 70, flows through distribution channel 50, tube 142, and outlet channel 152, and is emitted from outlet piece 147 for inhalation by the test subject. Providing distribution channel 50 that is independent of the other distribution channels 52, 54 defined in distribution block 46 prevents cross-contamination from occurring when gas stimuli is passing through distribution block 46. The volume of gas stimulus 74 emitted for each impact imposed by an actuator is constant and repeatable given the repeatable nature of the impact generated by each of actuators 82, 84, 86. In one example, the volume of stimulus that is emitted from outlet piece 147 for each impact by an actuator is at most 15 milliliters; otherwise the impacted bottle may take too long to recover from its temporarily deformed state. The impact delivered by the selected actuator is relatively quick, such as less than 0.1 seconds, and preferably about 0.071 seconds, and the velocity of the emitted gas stimuli is relatively high, for example, approximately 30 miles per hour. The actuator impact and resulting velocity is relatively quick to avoid potential adaptation to the gas stimulus by the test subject. Continuing with the example provided above, after bottle 60 is impacted and gas stimulus is emitted from outlet channel 152 of outlet piece 147, the same actuator 82 or the other actuators 84, 86 may be provided an actuation signal by computing device 92 to emit other gas stimuli from outlet piece 147. It should be understood that manual switches may be used to control actuators 82, 84, 86 instead of using computing device 92 as described above.

Figure 6:
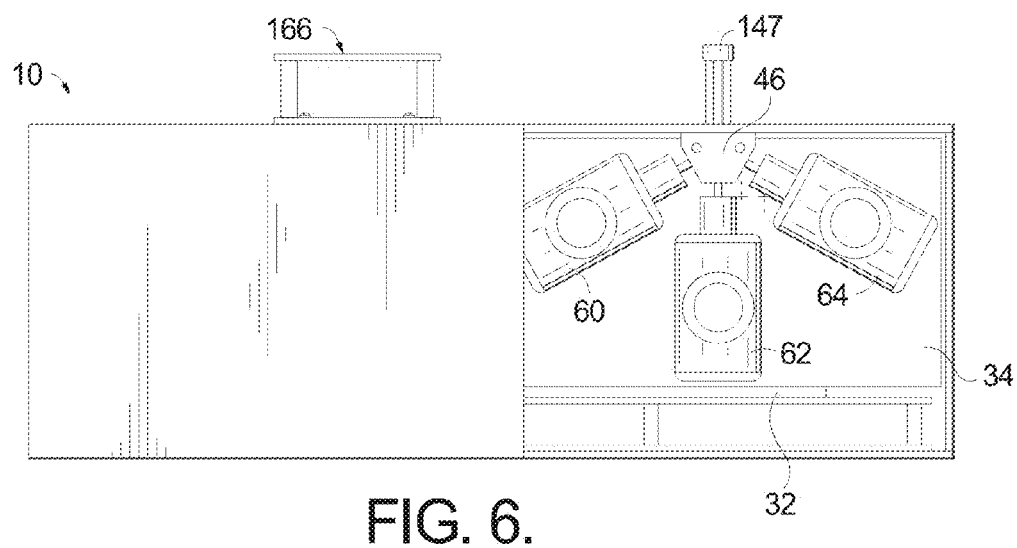
FIG. 6 is a rear view showing the carrier assembly in a loading position.
Figure 7:
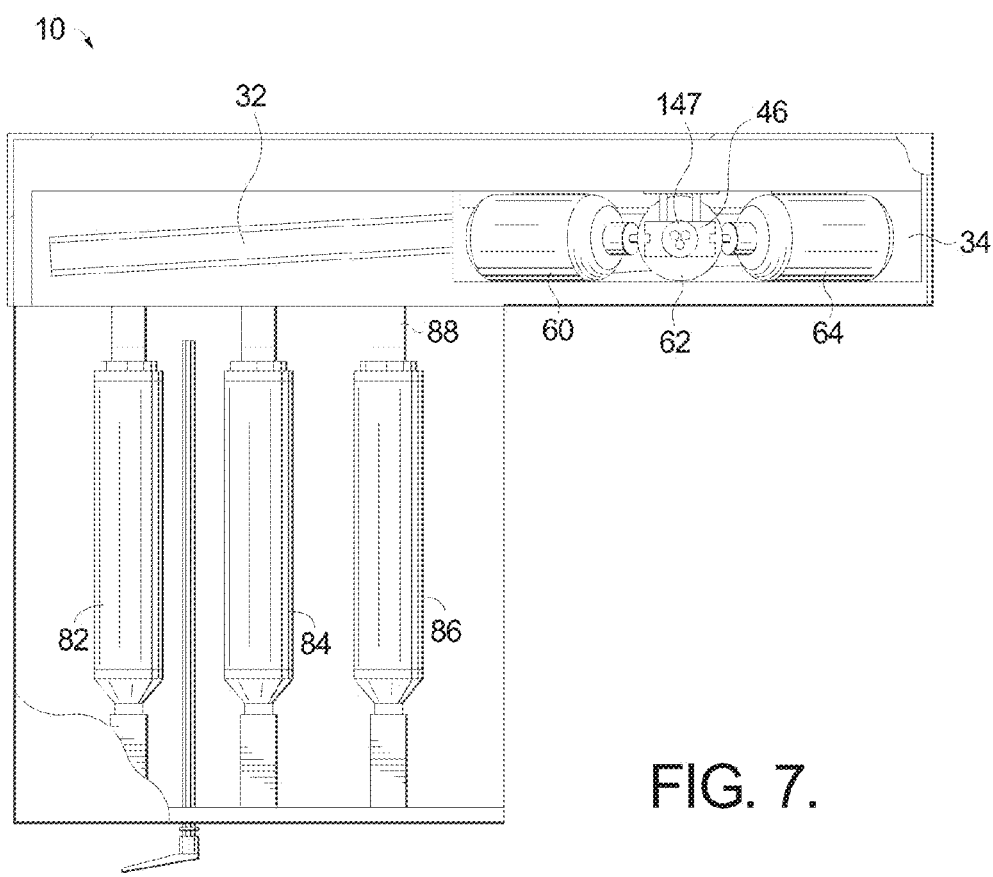
FIG. 7 is a top view showing the carrier assembly in the loading position.
Figure 10:
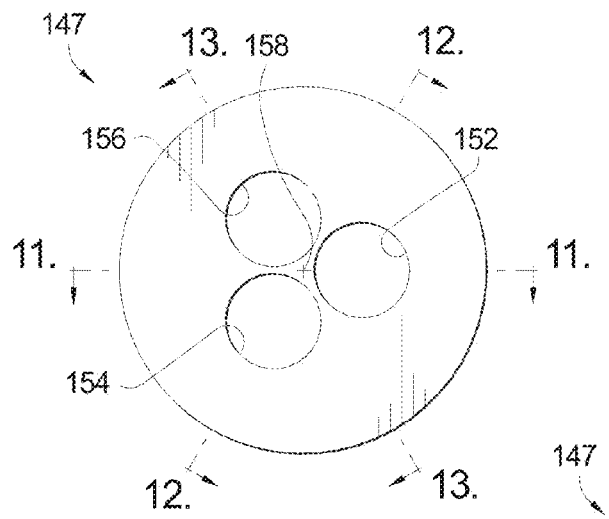
FIG. 10 is a top view of the outlet piece in accordance with another aspect of the present invention.
Figure 11:
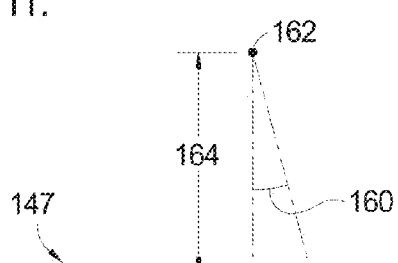
FIG. 11 is a cross-sectional view of the outlet piece taken along line 11-11 in FIG. 10.
Figure 12:
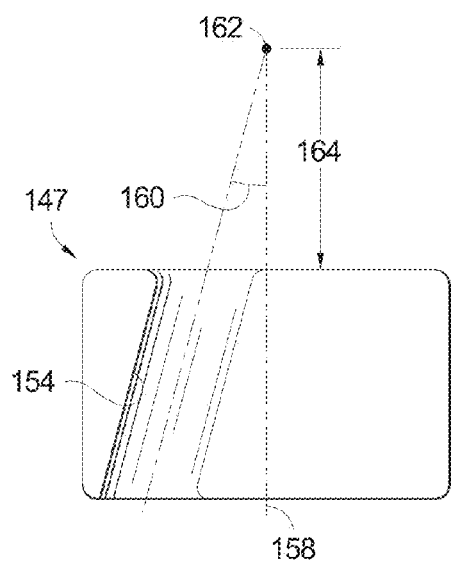
FIG. 12 is a cross-sectional view of the outlet piece taken along line 12-12 in FIG. 10.
Figure 13:
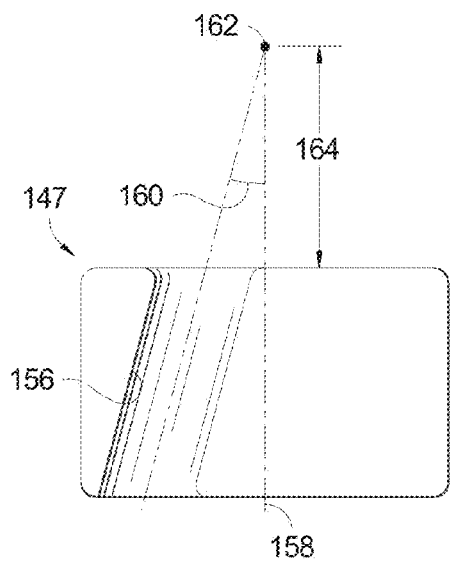
FIG. 13 is a cross-sectional view of the outlet piece taken along line 13-13 in FIG. 10.
Figure 14:
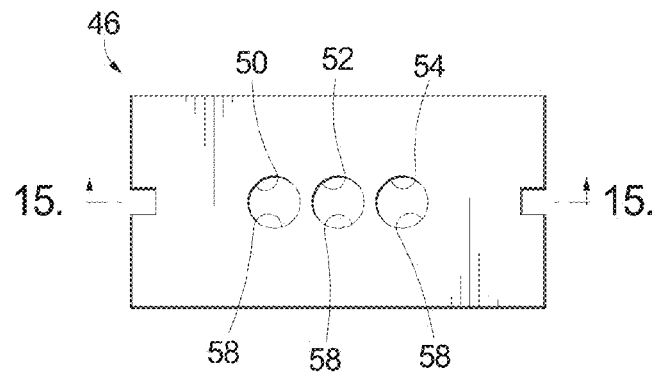
FIG. 14 is a top view of the distribution block in accordance with another aspect of the present invention.
Figure 15:
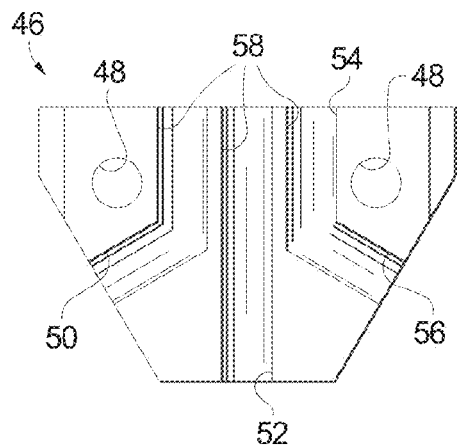
FIG. 15 is a cross-sectional view of the distribution block taken along line 15-15 in FIG. 14.
Figure 16:
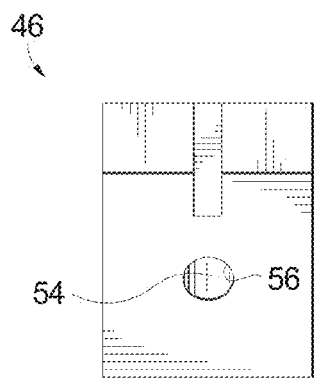
FIG. 16 is a side view of the distribution block shown in FIG. 14.
Figure 17:
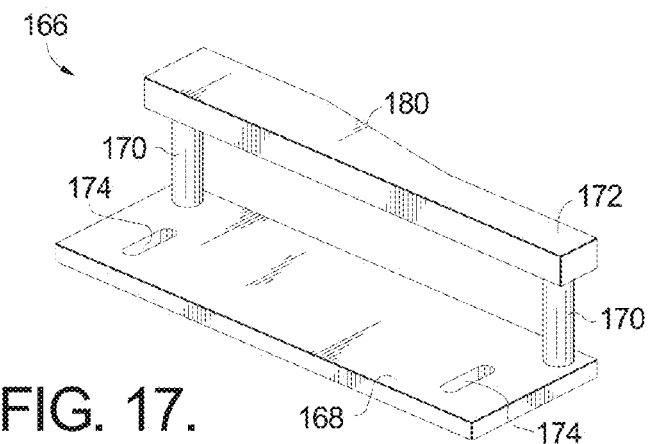
FIG. 17 is a perspective view of an assembly in accordance with another aspect of the present invention.
Figure 18:
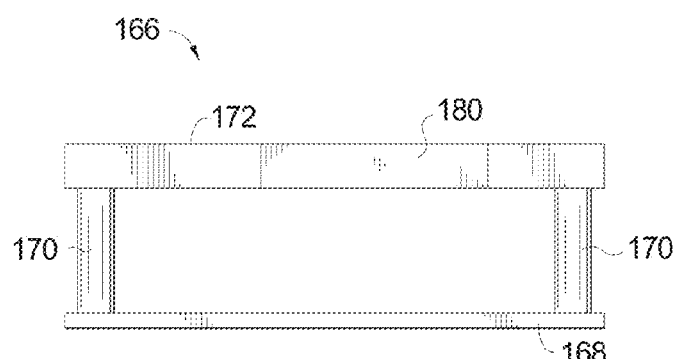
FIG. 18 is a front view of the assembly shown in FIG. 17.
Figure 19:
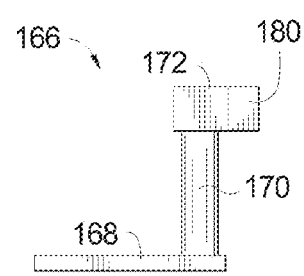
FIG. 19 is a right side view of the assembly shown in FIG. 17.
Figure 20:
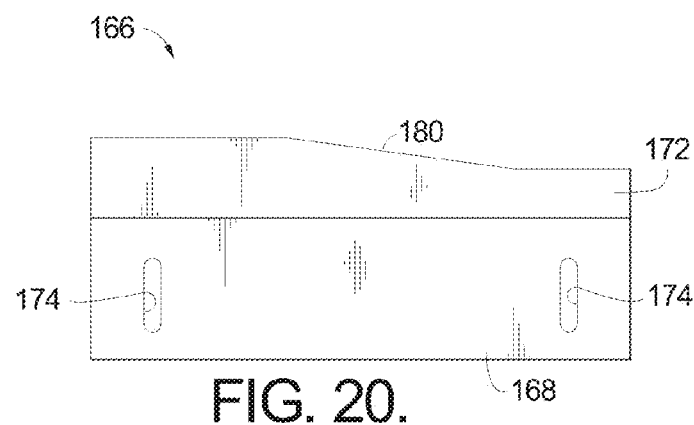
FIG. 20 is a top view of the ear assembly shown in FIG. 17.

After a specified testing sequence is complete, locking pin 42 can be moved to an unlocked position and carrier assembly 34 may be moved back to the first loading position, as best seen in FIGS. 6 and 7. Bottles 60, 62, 60 may then be easily removed from distribution block 46, and either refilled with volatile aromatic solution or replaced with new bottles and then filled with volatile aromatic solution. Tubes 142, 144, 146 may also be easily removed from distribution block 46 and outlet piece 147, and either cleaned or replaced with new tubes. The ease at which the bottles and tubes can be replaced prevents cross-contamination when using different gas stimuli and allows the testing process to be managed in an efficient manner.

Figure 24:
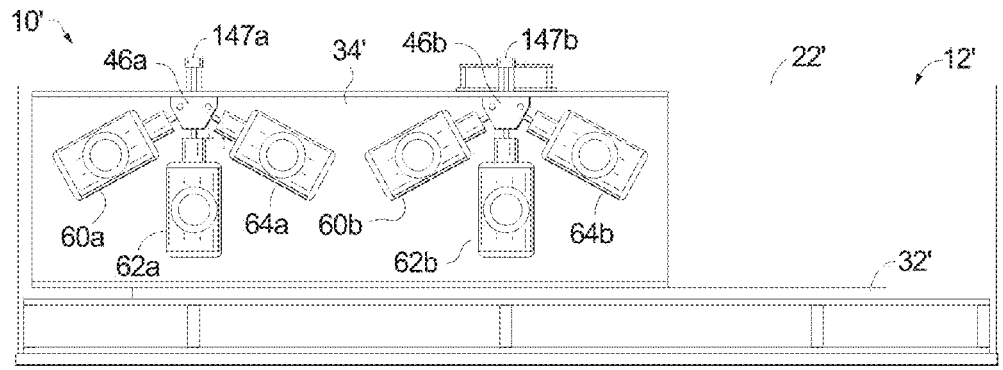
FIG. 24 is a back view of the olfactometer shown in FIG. 21 in the testing position.

As best seen in FIGS. 21-24, an alternative olfactometer 10' may be provided in accordance with another aspect of the present invention. The components and operation of olfactometer 10' are similar in many regards to olfactometer 10, and these common features will not be repeated herein. One difference in olfactometer 10' is that carrier assembly 34' is configured to allow two distribution blocks 46a, 46b to be mounted thereto, which in turn allows a first set of bottles 60a, 62a, 64a and a second set of bottles 60b, 62b, 64b to be used. As previously described, carrier assembly 34' is slidably disposed on a track 32' so that carrier assembly 34' is able to be moved between a first position (FIG. 22) and a second position (FIG. 24). With respect to olfactometer 10', track 32' is preferably disposed parallel to front wall 14' of housing 12', instead of at an angle as in olfactometer 10. In this aspect of the invention, in the first position as seen in FIG. 22, olfactometer 10' is capable of conducting the testing process in an efficient manner by allowing the second set of bottles 60b, 62b, 64b to be replaced and/or loaded with volatile aromatic solution while at the same time first set of bottles 60a, 62a, 64a are positioned adjacent to actuators 82, 84, 86 and being used for testing purposes. Further, in the second position as seen in FIG. 24, first set of bottles 60a, 62a, 64a may be replaced and/or loaded with volatile aromatic solution while the second set of bottles 60b, 62b, 64b are positioned adjacent to actuators 82, 84, 86 and being used for testing purposes.

Figure 25:
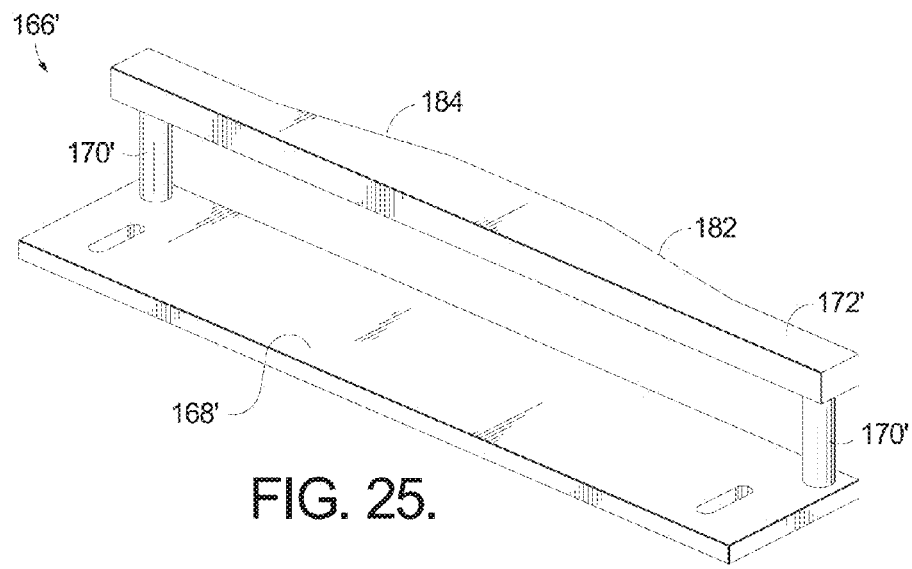
FIG. 25 is a perspective view of an assembly in accordance with another aspect of the present invention.
Figure 26:
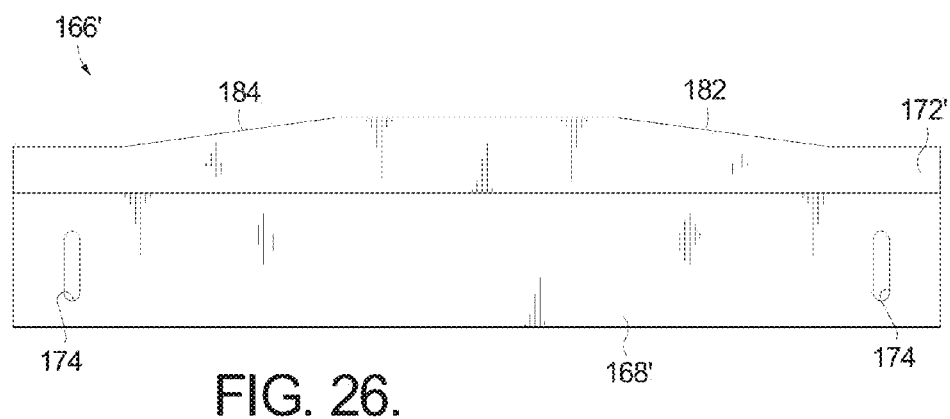
FIG. 26 is a top view of the assembly shown in FIG. 25.

As best seen in FIGS. 21, 25, and 26, an alternate assembly 166' is provided. Given that outlet pieces 147a, 147b approach assembly 166' from different directions as carrier assembly 34' is moved between first and second positions, the single tapered surface 180 provided on assembly 166 may not be adequate for use with olfactometer 10'. As such, assembly 166' comprises a base plate 168', at least one upstanding support 170', and a portion 172'. As described above with respect to assembly 166, base plate 168' is configured for being mounted to top wall 22' of housing 12', and at least one elongated slot 174 defined therein configured for receiving a fastener 176 (FIG. 1) for adjustably mounting assembly 166' on the top wall 22' of housing 12'. As best seen in FIG. 25, the at least one support 170' is coupled with base plate 168' and is adapted to position portion 172' at a height above top wall 22' of housing 12' so that portion 172' can either be slidably engaged with an outer surface 178 of outlet piece 147a as carrier assembly 34' is moved toward the first position (FIG. 22), or engaged with an outer surface 178 of outlet piece 147b as carrier assembly 34' is moved toward the second position (FIG. 24). In particular and with additional reference to FIGS. 25 and 26, as the carrier assembly 34' is moved toward the second position, outer surface 178 of outlet piece 147b is placed in contact with a tapered surface 184 that is angled such that the associated tubes bend slightly and outlet piece 147b moves toward the test subject's nose. Similarly, as carrier assembly 34' is moved toward the first position, outer surface 178 of outlet piece 147a is placed in contact with a tapered surface 182 that is angled such that the associated tubes bend slightly and outlet piece 147a moves toward the test subject's nose.

By utilizing a multi-modal olfactometer, as described above, a number of advantages are realized while at the same time overcoming some of the drawbacks that are present with current devices in the field. For example, while existing dilution olfactometers are capable of conducting olfactory testing on test subjects, the present olfactometer 10, 10' is capable of doing so with greater speed, accuracy and reproducibility. Olfactometer 10, 10' eliminates the need to design a machine with complicated plumbing schemes and valve components which exists with dilution olfactometers by using a head space in equilibrium with a liquid volatile aromatic solution so there is already a steady concentration of gas stimulus present in the bottle before the gas stimulus is emitted from the outlet piece. Furthermore, the short flow path the gas stimulus travels in olfactometer 10, 10' provides for a fast (less than 0.1 seconds) delivery of gas stimulus to the test subject. Furthermore, both the material selection of the bottles and tubes, as well as the dedicated, independent, and short paths through the distribution block and outlet piece, practically eliminate the opportunity for cross-contamination either within the gas stimulus flow path or between bottles. The olfactometer 10, 10' also allows for the testing of multiple materials in one setup, and to alternate between samples and/or bottles in a way that prevents the test subject from guessing which sample is being presented. Based on the speed at which the gas stimuli is presented to the test subject, combined with the use of visual and/or audio cues to notify the test subject when to inhale the gas stimulus through his or her nose, coordination between the release of the gas stimulus from the outlet piece and inhalation is provided, ensuring a repeatable intake of the sample presented.

The foregoing description of the preferred embodiment of the invention has been presented for the purpose of illustration and description. It is not intended to be exhaustive nor is it intended to limit the invention to the precise form disclosed. It will be apparent to those skilled in the art that the disclosed embodiments may be modified in light of the above teachings. The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

The invention claimed is:

1. A device for selectively discharging a gas stimulus to a test subject, the device comprising:
   a track;
   a carrier assembly slidably coupled with the track, wherein the carrier assembly is configured for moving between a first position and a second position;
   a distribution block coupled with the carrier assembly, wherein the distribution block includes a first distribution channel and a second distribution channel defined therein, wherein each of the first and second distribution channels include an inlet opening and an outlet opening, and wherein the first distribution channel is independent of the second distribution channel;
   a first bottle configured for containing a first gas stimulus, wherein the first bottle includes an outlet opening configured for being coupled with the inlet opening of the first distribution channel;

a second bottle configured for containing a second gas stimulus, wherein the second bottle includes an outlet opening configured for being coupled with the inlet opening of the second distribution channel;

a first tube including a first end and a second end, wherein the first end of the first tube is connected to the outlet opening of the first distribution channel of the distribution block;

a second tube including a first end and a second end, wherein the first end of the second tube is connected to the outlet opening of the second distribution channel of the distribution block;

an outlet piece including a first outlet channel and a second outlet channel defined therein, wherein the first outlet channel is independent of the second outlet channel, wherein the second end of the first tube is connected to the first outlet channel of the outlet piece, and wherein the second end of the second tube is connected to the second outlet channel of the outlet piece; and at least one actuator positioned adjacent to the first and second bottles when the carrier assembly is in the second position, wherein the at least one actuator is configured for selectively impacting either the first or second bottle when the carrier assembly is in the second position, wherein when the first bottle is impacted by the at least one actuator, the first gas stimulus flows through each of the first distribution channel in the distribution block, the first tube, and the first outlet channel in the outlet piece for inhalation by test subject, and wherein when the second bottle is impacted by the at least one actuator, the second gas stimulus flows through each of the second distribution channel in the distribution block, the second tube, and the second outlet channel in the outlet piece for inhalation by the test subject.

2. A device in accordance with claim 1, wherein the at least one actuator is a first actuator and a second actuator, wherein the first actuator is positioned adjacent to the first bottle when the carrier assembly is in the second position, and wherein the second actuator is positioned adjacent to the second bottle when the carrier assembly is in the second position.

3. A device in accordance with claim 2, further comprising:
a computing device including a memory, wherein the computing device is in communication with both the first and second actuators; and
an application program stored in the memory of the computing device, wherein the application program is configured for transmitting an actuation signal to one of the first actuator or the second actuator to selectively impact the respective first or second bottle.

4. A device in accordance with claim 3, wherein the computing device further includes a monitor, wherein the application program is further configured for providing at least one visual cue using the monitor prior to transmitting the actuation signal to the one of the first actuator or the second actuator.

5. A device in accordance with claim 4, wherein the computing device further includes a speaker, wherein the application program is further configured for providing at least one audio cue using the speaker prior to transmitting the actuation signal to the one of the first actuator or the second actuator.

6. A device in accordance with claim 1, wherein the at least one actuator impacts either the first or second bottle for less than 0.1 seconds.

7. A device in accordance with claim 6, wherein the at least one actuator impacts either the first or second bottle for about 0.071 seconds.

8. A device in accordance with claim 1, wherein the outlet piece includes a longitudinal axis, and wherein each of the first and second outlet channels defined in the outlet piece are disposed at about a 15 degree angle relative to the longitudinal axis.

9. A device in accordance with claim 1, further comprising a housing including a front wall, wherein the track is coupled to the housing and positioned at an angle relative to the front wall of the housing.

10. A device in accordance with claim 9, wherein the track is positioned at about a 3 degree angle relative to the front wall of the housing.

11. A device in accordance with claim 1, further comprising a housing including a top wall, wherein an elongated slot is defined in the top wall, and wherein the first and second tubes extend through the elongated slot.

12. A device in accordance with claim 1, further comprising:
a housing:
a locking pin slidably coupled with the housing, wherein the locking pin is positioned to selectively engage the carrier assembly when the carrier assembly is in the second position.

13. A device in accordance with claim 1, further comprising:
a housing including a top wall;
an assembly mounted on the top wall of the housing, wherein the assembly is adjustably positioned to engage the outlet piece when the carrier assembly is moved toward the second position.

14. A device in accordance with claim 13, wherein the assembly comprises:
a base plate configured for being mounted to the top wall of the housing;
a support coupled with the base plate; and
a portion coupled with the support, wherein the portion includes a first tapered surface configured for engaging the outlet piece when the carrier assembly is moved toward the second position.

15. A device in accordance with claim 14, wherein the base plate has at least one elongated slot defined therein configured for receiving a fastener for adjustably mounting the assembly on the top wall of the housing.

16. A device in accordance with claim 1, further comprising at least one mounting pin extending from the carrier assembly, wherein the distribution block includes a corresponding number of apertures configured for receiving the at least one mounting pin to couple the distribution block to the carrier assembly.

17. A device in accordance with claim 1, wherein the first bottle and the second bottle are directly connected to the distribution block.

18. A device in accordance with claim 1, wherein at least one of the first bottle and the second bottle are formed of perfluoroalkoxy alkane (PFA).

19. A device in accordance with claim 1, wherein at least one of the first tube and the second tube are formed of perfluoroalkoxy alkane (PFA).

20. A device in accordance with claim 1, wherein the first gas stimulus and the second gas stimulus are different.

21. A device in accordance with claim 1, wherein the distribution block includes a third distribution channel defined therein, wherein the third distribution channel includes an inlet opening and an outlet opening, wherein the third distribution channel is independent of the first and second distribution channels,
- wherein the device further comprises a third bottle configured for containing a third gas stimulus, wherein the third bottle includes an outlet opening configured for being coupled with the inlet opening of the third distribution channel,
- wherein the device further comprises a third tube including a first end and a second end, wherein the first end of the third tube is connected to the outlet opening of the third distribution channel of the distribution block,
- wherein the outlet piece includes a third outlet channel defined therein, wherein the third outlet channel is independent of the first and second outlet channels, wherein the second end of the third tube is connected to the third outlet channel of the outlet piece, and
- wherein the at least one actuator is positioned adjacent to the third bottle when the carrier assembly is in the second position, and wherein the at least one actuator is configured for selectively impacting either the first, second or third bottle when the carrier assembly is in the second position,
- wherein when the third bottle is impacted by the at least one actuator, the third gas stimulus flows through each of the third distribution channel in the distribution block, the third tube, and the third outlet channel in the outlet piece for inhalation by the test subject.

22. A device in accordance with claim 21, wherein two of the first gas stimulus, the second stimulus, and the third gas stimulus are the same.

23. A device in accordance with claim 1, wherein the distribution block is a first distribution block, wherein the outlet piece is a first outlet piece, and wherein the device further comprises:
- a second distribution block coupled with the carrier assembly, wherein the second distribution block includes a third distribution channel and a fourth distribution channel defined therein, wherein each of the third and fourth distribution channels of the second distribution block include an inlet opening and an outlet opening, and wherein the third distribution channel of the second distribution block is independent of the fourth distribution channel of the second distribution block;
- a third bottle configured for containing a third gas stimulus, wherein the third bottle includes an outlet opening configured for being coupled with the inlet opening of the third distribution channel of the second distribution block;
- a fourth bottle configured for containing a fourth gas stimulus, wherein the fourth bottle includes an outlet opening configured for being coupled with the inlet opening of the fourth distribution channel of the second distribution block;
- a third tube including a first end and a second end, wherein the first end of the third tube is connected to the outlet opening of the third distribution channel of the second distribution block;
- a fourth tube including a first end and a second end, wherein the first end of the fourth tube is connected to the outlet opening of the fourth distribution channel of the second distribution block; and
- a second outlet piece including a third outlet channel and a fourth outlet channel defined therein, wherein the third outlet channel of the second outlet piece is independent of the fourth outlet channel of the second outlet piece, wherein the second end of the third tube is connected to the third outlet channel of the second outlet piece, and wherein the second end of the fourth tube is connected to the fourth outlet channel of the second outlet piece,
- wherein when the carrier assembly is in the first position, the at least one actuator is positioned adjacent to the third and fourth bottles, wherein the at least one actuator is configured for selectively impacting either the third or fourth bottle when the carrier assembly is in the first position,
- wherein when the third bottle is impacted by the at least one actuator, the third gas stimulus flows through each of the third distribution channel in the second distribution block, the third tube, and the third outlet channel in the second outlet piece for inhalation by the test subject, and
- wherein when the fourth bottle is impacted by the at least one actuator, the fourth gas stimulus flows through each of the second distribution channel in the distribution block, the fourth tube, and the fourth outlet channel in the outlet piece for inhalation by the test subject.

24. A device in accordance with claim 23, further comprising:
- a housing including a top wall;
- an assembly mounted on the top wall of the housing, wherein the assembly is selectively positioned to engage the first outlet piece when the carrier assembly is moved toward the second position and engage the second outlet piece when the carrier assembly is moved toward the first position.

25. A device in accordance with claim 24, wherein the assembly comprises:
- a base plate configured for being mounted to the top wall of the housing;
- a support coupled with the base plate; and
- a portion coupled with the support, wherein the portion includes a first tapered surface configured for engaging the first outlet piece when the carrier assembly is moved toward the second position, and wherein the portion includes a second tapered surface configured for engaging the second outlet piece when the carrier assembly is moved toward the first position.

26. A device in accordance with claim 25, wherein the base plate has at least one elongated slot defined therein configured for receiving a fastener for adjustably mounting the assembly on the top wall of the housing.

* * * * *